United States Patent
Frischke et al.

(10) Patent No.: US 10,944,168 B2
(45) Date of Patent: Mar. 9, 2021

(54) MEDICAL DEVICE

(71) Applicant: Berlin Heart GmbH, Berlin (DE)

(72) Inventors: Michael Frischke, Rangsdorf (DE); Kim Peter Winterwerber, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 262 days.

(21) Appl. No.: 15/710,149

(22) Filed: Sep. 20, 2017

(65) Prior Publication Data

US 2018/0131086 A1    May 10, 2018

(30) Foreign Application Priority Data

Sep. 22, 2016 (EP) .................................. 16190243

(51) Int. Cl.
| | |
|---|---|
| *H01Q 1/52* | (2006.01) |
| *A61M 1/10* | (2006.01) |
| *H01Q 1/27* | (2006.01) |
| *H01Q 1/42* | (2006.01) |

(52) U.S. Cl.
CPC .......... *H01Q 1/526* (2013.01); *A61M 1/1086* (2013.01); *H01Q 1/273* (2013.01); *H01Q 1/42* (2013.01); *A61M 2205/3523* (2013.01); *A61M 2205/3561* (2013.01); *A61M 2205/3592* (2013.01)

(58) Field of Classification Search
CPC ........ A61M 1/1086; A61M 2205/3523; A61M 2205/3561; A61M 2205/3592; A61M 2205/3507; H01Q 1/273; H01Q 1/42; H01Q 1/526
See application file for complete search history.

(56) References Cited

U.S. PATENT DOCUMENTS

| | | | | |
|---|---|---|---|---|
| 8,608,635 | B2* | 12/2013 | Yomtov | A61M 1/10 |
| | | | | 600/17 |
| 2008/0319544 | A1 | 12/2008 | Yaegashi | |
| 2010/0168818 | A1* | 7/2010 | Barror | A61N 1/025 |
| | | | | 607/60 |
| 2015/0290373 | A1* | 10/2015 | Rudser | A61M 1/1086 |
| | | | | 623/3.27 |
| 2016/0030652 | A1 | 2/2016 | Arndt et al. | |

FOREIGN PATENT DOCUMENTS

| | | | |
|---|---|---|---|
| WO | WO 2011/073334 A1 | 6/2011 | |
| WO | WO-2011073334 A1 * | 6/2011 | ......... A61N 1/36125 |
| WO | WO 2014/161978 A1 | 10/2014 | |

* cited by examiner

*Primary Examiner* — Michael W Kahelin
*Assistant Examiner* — Vynn V Huh
(74) *Attorney, Agent, or Firm* — Brinks Gilson & Lione

(57) ABSTRACT

A medical apparatus is provided that includes an implantable element, in particular a heart pump, and a control unit for the implantable element, which control unit is connected to the implantable element by means of a first connection. The problem of arranging an antenna of a radio module on the control unit expediently and favourably is solved in that the control unit is configured for arrangement outside the patient's body and has a predetermined orientation relative to the patient's body and has a radio module, wherein an antenna of the radio module is arranged in such a way that the region in which the patient's body is intended to be positioned, as considered from the control unit, is shielded from the antenna at least in part by electromagnetically shielding, in particular electrically conductive parts of the control unit or housing thereof.

13 Claims, 5 Drawing Sheets

Fig. 2

MEDICAL DEVICE

CROSS-REFERENCE TO RELATED APPLICATIONS

This application claims priority under 35 USC § 119 to European patent application EP 16 190 243.2 filed on Sep. 22, 2016.

BRIEF DESCRIPTION OF THE DRAWINGS

FIG. 13 a control unit with a radio module that can be plugged in;

DETAILED DESCRIPTION

Figure 1:
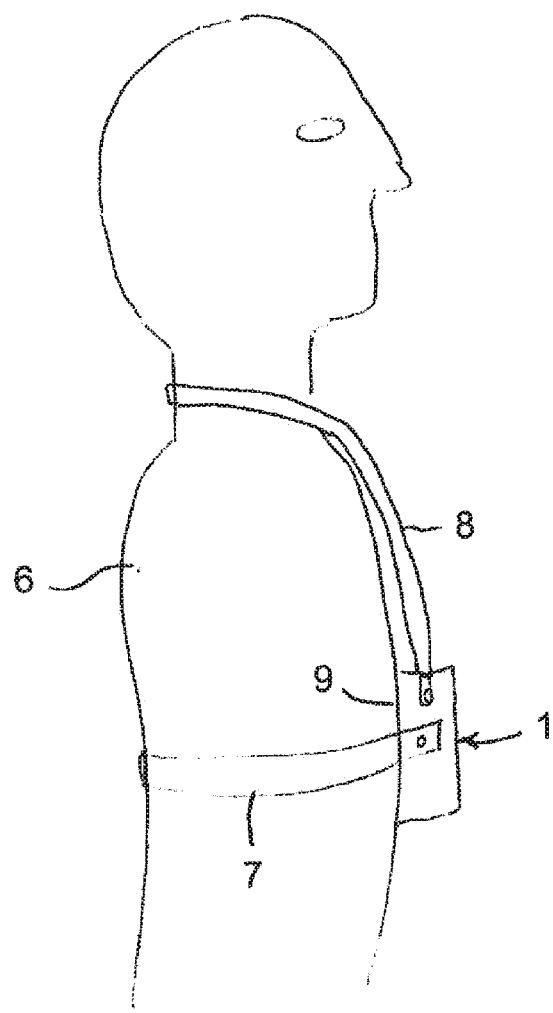
FIG. 1 a control unit of a medical apparatus on a patient's body.

The invention lies in the field of mechanics and mechanical engineering and can be used particularly advantageously in the field of medical engineering. More specifically, the invention relates to a medical apparatus with an implantable element, which is connected to a control unit, which for example can be arranged outside a patient's body.

Control units of this kind allow the implantable element to be controlled in an increasingly detailed manner as technology advances, wherein a more sophisticated control is usually also accompanied by an enhanced sensor system at the patient's body. The implantable elements to some extent also allow a large number of operating modes and control possibilities.

A communication interface, which is often designed as a radio interface with the aid of a radio module, is required at control units of this kind for many purposes, such as external access to the control unit, software updates and communication in general with other apparatuses. When equipping a medical apparatus with a radio module, however, particular requirements must be considered, since transmission through the patient's body and thereinto should be avoided for health reasons and due to potential interferences with implanted elements. In addition, the best-possible, interference-free communication to an external transceiver should be established, with minimal transmission power and minimised damping of the radio signals.

The present innovation, against the background of the prior art, therefore addresses the problem of creating a medical apparatus of the type described in the introduction, the control unit of which allows optimised communication over a radio interface.

A further important constraint is constituted by the strict EMC requirements. Faraday cages are therefore often necessary in order to protect the control electronics. The challenge then lies in implementing a radio link such that the EMC protection is not lost, but good transmission and receiving properties are still achieved.

The innovation relates accordingly to a medical apparatus with an implantable element, in particular a heart pump, and a control unit for the implantable element, which control unit is connected to the implantable element by means of a first connection. A particularly good communication of the control unit with elements arranged outside the apparatus by means of a radio module is provided in that the control unit is configured for arrangement outside the patient's body and a predetermined orientation relative to the patient's body and has a radio module, wherein an antenna of the radio module is arranged in such a way that the region in which the patient's body is intended to be positioned, as considered from the control unit, is shielded from the antenna at least in part by electromagnetically shielding, in particular electrically conductive parts of the control unit or housing thereof.

The antenna of the radio module is thus arranged in such a way that the emitted electromagnetic radiation, when the controller is carried on the patient's body, does not strike the patient's body or only strikes it to a small extent. Either the control unit itself, for example in the form of circuit boards or electronic components, or parts of the housing of the control unit are designed in such a way that they for example are electrically conductive or contain electrically conductive elements and thus largely shield electromagnetic radiation. The antenna of the radio module is arranged on the side of these shielding parts facing away from the patient's body, such that the electromagnetic radiation does not penetrate through the patient's body more strongly than is necessary.

The control unit is configured in one embodiment in such a way that it can be arranged on and fastened to the outside of the patient's body. For example, it can be flat or convex on the side facing towards the body. The edges and/or corners of the housing can be rounded. The control unit can be able to be glued to the patient's body or can be able to be fastened thereto using a self-adhesive hook-and-loop means. Eyelets or tabs or openings for guiding or fastening one or more straps, tapes, flat belts or other strip-like fastening means can be provided on the housing of the control unit.

The control unit can be formed in such a way that in the operating position on the patient's body its height perpendicular to the contact face against the patient's body is smaller than the maximum dimensions of extent perpendicular to this direction, for example half the height, a quarter or a sixth of these dimensions of extent. In other words, the control unit lies flat against the patient's body.

The control unit can be rectangular, apart from rounded portions of the housing. An electrically insulating part of the housing can also be at least in part elastic and for example can also be made at least in part of an elastomer. Furthermore, the housing is preferably liquid-tight.

Here, in one implementation, it can be provided that the antenna is positioned and oriented in such a way that the influence of a patient's body in the operating state on the emission characteristic of the antenna is minimised, in particular in that the maximum of the emission intensity from the antenna is arranged in a direction which does not touch/contact the position of the patient's body. The orientation of the antenna can be provided so that, as considered from the antenna, less than 50%, advantageously less than 20%, more advantageously less than 10% of the emitted transmission power penetrates the region intended for the patient's body.

For example, it can be provided that the control unit has an at least partially electrically conductive housing. The housing of the control unit for example can be made at least in part of sheet steel or aluminium and can be produced either from one piece by casting or deep drawing or can be assembled from a number of planar elements. A housing of this kind of the control unit is usually produced so as to be liquid-tight, so that, in the event that it is joined together from a number of parts, the joins are sealed.

Here, apart from the liquid tightness, it can also be desirable to provide a tightness with respect to electromagnetic waves from the viewpoint of electromagnetic compatibility. For example, joining materials or elastomer seals used therein can be interspersed with conductive particles in order to ensure an electromagnetic tightness.

The electromagnetically shielding parts of the housing can also be formed for example as plastic parts, wherein the plastic must be sufficiently filled with conductive particles.

It can also be provided in one embodiment that the antenna is arranged at least in part within the housing of the control unit behind a region of the housing permeable for radio signals or behind a window-like recess of the housing. In this case, the housing of the control unit is not made entirely of an electrically conductive material, and instead regions are provided in which the housing is made of a material permeable for radio signals/electromagnetic waves or has a window opening. Such a part of the housing can be provided for example as a housing lid or as a closure for a housing opening. A window for electromagnetic waves is thus created, behind which the antenna for emission of radio signals can be arranged.

In one embodiment it can also be provided that the antenna is arranged at least in part outside the housing of the control unit. In this case the housing does not need to have any regions permeable for electromagnetic waves, and instead merely a feedthrough for the antenna line. The antenna itself can then be arranged externally insulated from the housing.

For example, it can be provided that the antenna runs at least sectionally substantially parallel to a housing edge of an electrically conductive housing part of the control unit, for example at a distance of at least 1 mm therefrom. At least a portion of the antenna can thus be provided parallel to a housing edge and at a distance of a few millimetres therefrom, but at a minimum distance from the housing, which limits the capacitance with respect to the housing and ensures the insulation strength with respect to the housing.

Different portions of the antenna can also run at an angle of 90° along different housing edges at a distance therefrom. It is thus ensured that the emission characteristic of the antenna enables an emission of the radio signals in all directions with a sufficient intensity.

In another embodiment it can also be provided that the antenna has the form of a dipole, in particular with two closed conductor loops or conductor faces. Dipole loops of this kind can be provided for example beneath an electrically insulating region of the housing permeable for electromagnetic waves, or can be integrated in housing parts of this kind. Such dipoles for example can be moulded in plastic parts of the housing.

A further embodiment for this purpose can provide, for example, that the housing of the control unit has at least one region which is made of an electrically insulating material permeable for electromagnetic waves.

As already explained in part above, it can also be provided that an antenna is arranged within the housing in or directly behind the region made of an electrically insulating material permeable for electromagnetic waves.

For example, a further embodiment can provide that the, or a, region made of an electrically insulating material permeable for electromagnetic waves surrounds the electrically conductive region of the housing fully or in part and/or is tightly joined to the electrically conductive region of the housing, in particular is glued, cast, or tightly connected by means of an elastomer seal. In this case, the antenna can lie for example outside the contour of the electrically conductive parts of the housing impermeable for electromagnetic waves, but within the contour of the parts of the housing permeable for electromagnetic waves and can thus be protected against influences from outside.

For example, the housing can also have a geometrically simple shape, for example a cuboid or cube shape, wherein only part is made of metal and part is made of plastic. The partition line between the part of the housing made of material impermeable for electromagnetic waves and the part made of material permeable for electromagnetic waves should be selected so that the patient's body is protected against the radio signals, but in particular also against electromagnetic waves emitted by other electrical parts of the control unit. If, for example, a motor controller is disposed in the control unit, it can have a power inverter drive with pulse width modulation, which performs high-frequency switching operations, wherein a relatively high amount of electromagnetic radiation is emitted by this controller. This radiation should also be shielded from the patient's body by the housing of the controller.

In a further embodiment it can also be provided, for example, that the, or a, region of the housing made of an electrically insulating material permeable for electromagnetic waves protrudes beyond the contour of the electrically conductive regions of the housing, wherein an antenna is arranged in the region protruding beyond the contour of the electrically conductive regions of the housing.

It can also be provided that the radio module can be plugged into a plug device on the housing of the control unit, wherein in particular the housing of the control unit has a recess for receiving the radio module at least in part, particularly completely. In this case, for example at least some of the volume of the radio module or the entire radio module can be received in the contour of the housing. For example, a plug connection for electrically connecting the radio module to the rest of the parts of the control unit can be provided within the recess for the radio module. The recess in the housing for example can be formed completely by a metallic housing wall, since the radio module itself can contain the antenna and is plugged to the housing outside the metallic parts thereof. However, the antenna can also be permanently connected to the housing of the control unit and electrically connected thereto only by plugging on the radio module. By means of the electrical plug connection of the radio module, said module on the one hand is supplied with energy from the interior of the housing by means of a power supply unit or a battery, and on the other hand it receives signals from the rest of the parts of the control unit and can forward these signals by means of its radio interface. On the other hand, the radio module can also receive signals from outside and can forward these to the other parts of the control unit.

Figure 2:
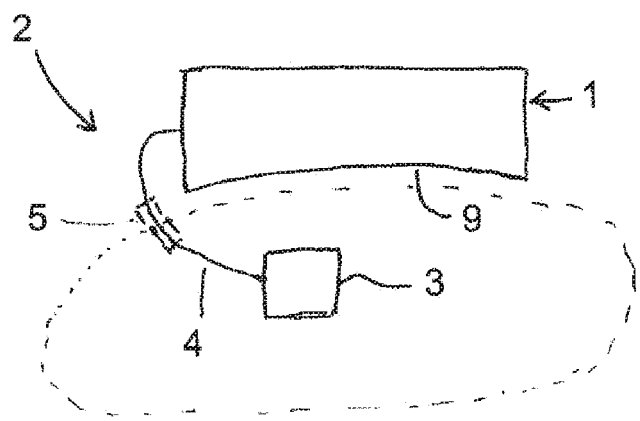
FIG. 2 a control unit and an implantable element of a medical apparatus.
Figure 3:
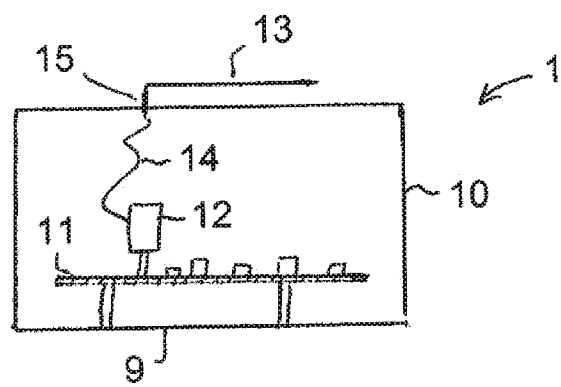
FIG. 3 a control unit with a housing and an external antenna.
Figure 4:
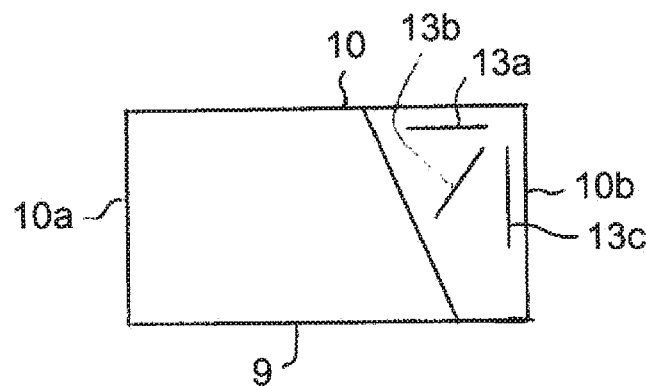
FIG. 4 a housing with a region permeable for electromagnetic waves and with an antenna.
Figure 5:
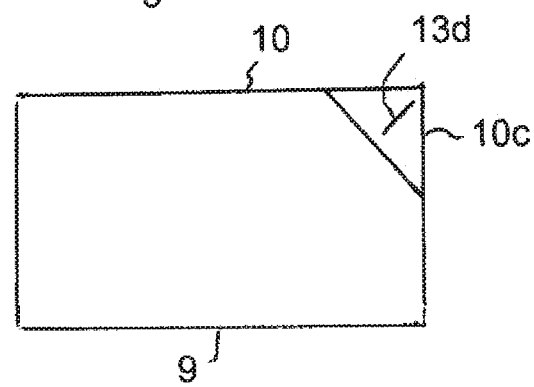
FIG. 5 a housing with a region permeable for electromagnetic waves and with an antenna.
Figure 6:
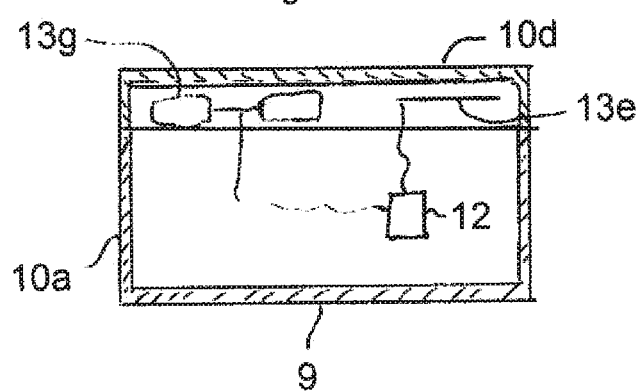
FIG. 6 a housing with a region permeable for electromagnetic waves and with an antenna.
Figure 7:
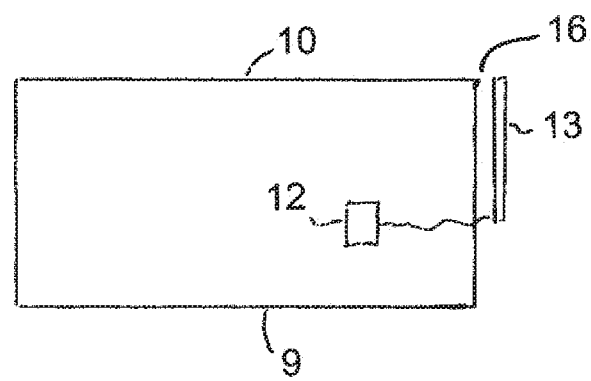
FIG. 7 a control unit with an antenna arranged outside the housing.
Figure 8:
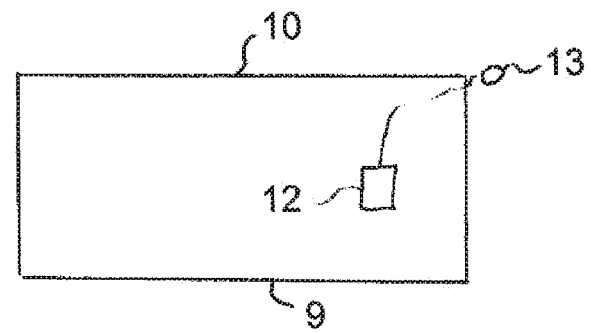
FIG. 8 a control unit with an antenna arranged outside the housing.
Figure 9:
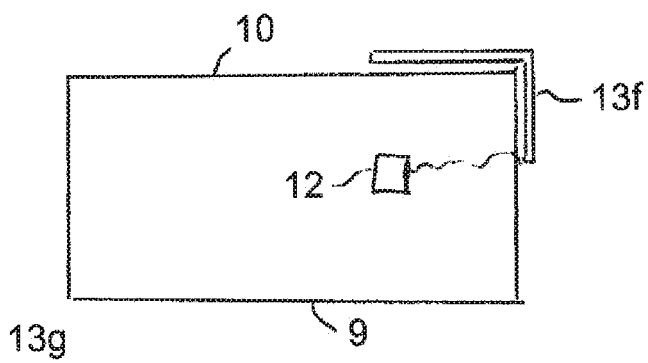
FIG. 9 a control unit with an antenna arranged outside the housing.
Figure 10:
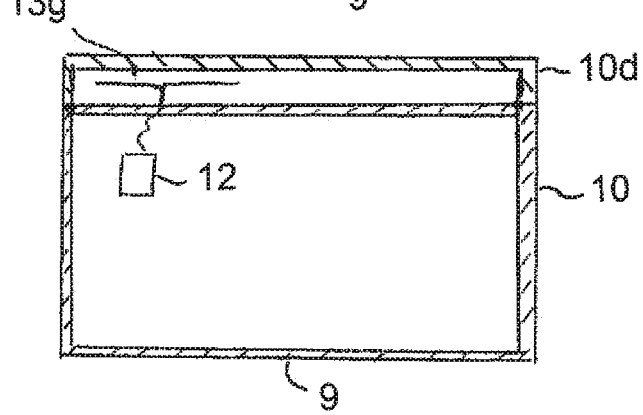
FIG. 10 a control unit with a housing which is additionally covered in part by an additional housing made of material permeable for electromagnetic waves, and an antenna arrangement.
Figure 11:
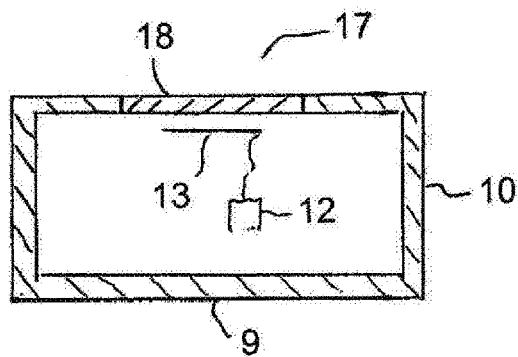
FIG. 11 a housing with a window opening permeable for electromagnetic waves, and an antenna arranged within the housing.
Figure 12:
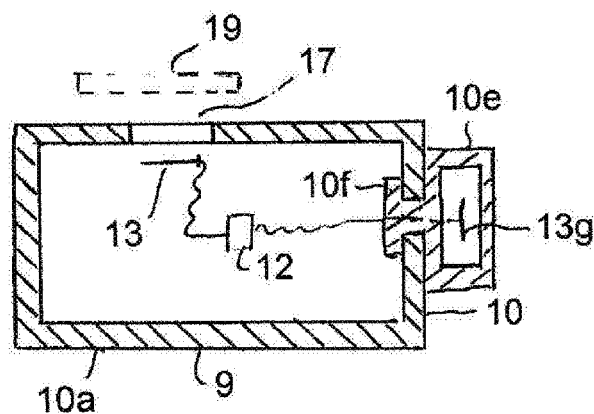
FIG. 12 a housing with a window opening permeable for electromagnetic waves, and an antenna arranged within the housing.
Figure 13:
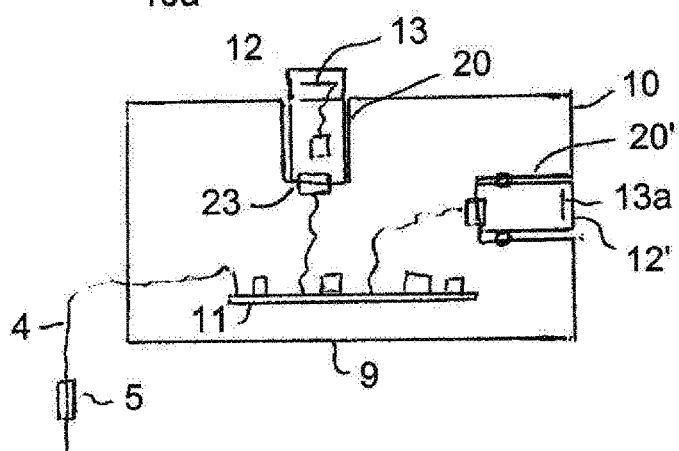
Figure 14:
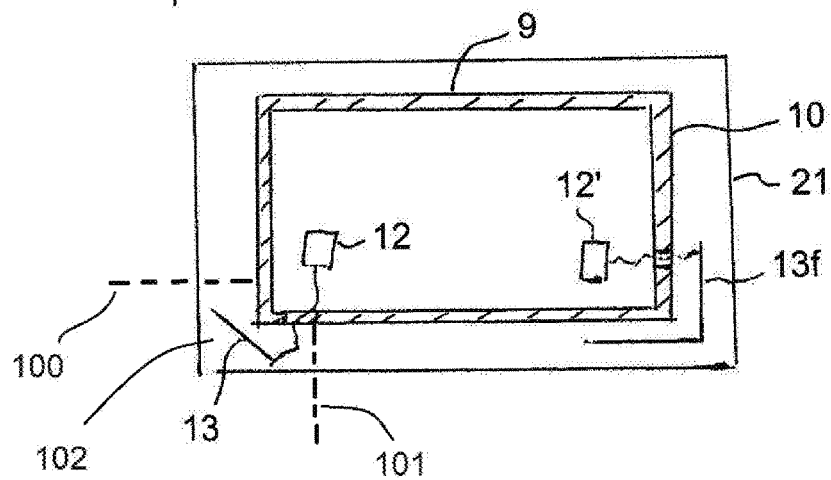
FIG. 14 a control unit with a first housing, which is completely surrounded by a second housing permeable for electromagnetic waves.
Figure 15:
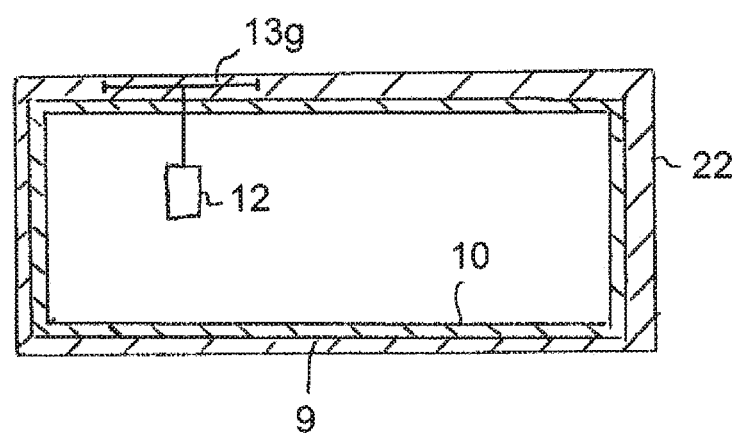
FIG. 15 a housing which is coated with a material permeable for electromagnetic waves, wherein an antenna is arranged in the coating.

The innovation will be presented hereinafter with reference to exemplary embodiments in figures of a drawing and will be explained below. In the figures:

FIG. 1 shows, in a side view, a control unit of a medical apparatus on a patient's body, FIG. 2 shows a control unit and an implantable element of a medical apparatus, FIG. 3 schematically shows a control unit with a housing and an external antenna, FIGS. 4, 5 and 6 each show a housing with a region permeable for electromagnetic waves and with an antenna, FIGS. 7, 8 and 9 each show a control unit with an antenna arranged outside the housing, FIG. 10 shows a control unit with a housing which is additionally covered in part by an additional housing made of material permeable for electromagnetic waves, and an antenna arrangement, FIGS. 11 and 12 each show a housing with a window opening permeable for electromagnetic waves, and an antenna arranged FIG. 13 shows a control unit with a radio module that can be plugged in, FIG. 14 shows a control unit with a first housing, which is completely surrounded by a second housing permeable for electromagnetic waves, and FIG. 15 shows a housing which is coated with a material permeable for electromagnetic waves, wherein an antenna is arranged in the coating.

FIG. 1 schematically shows, in a side view, a patient's body 6 with a control unit 1, which the patient carries on their body and which is held by two carry straps 7, 8 indicated by way of example. The control unit is designed and connected to the straps 7, 8 in such a way that the side 9 of the control unit 1 lying against the patient's body 6 is fixed. The side 9 of the control unit 1 can also be designed to rest against the patient's body by other measures, for example a particular marking or coating. In addition, the shaping of the side 9 of the control unit can additionally be adjusted in a complementary manner to the shape of the patient's body, for example in that the side 9 is concave in at least one plane, in particular also two planes.

The control unit 1 is connected to an implantable element 3 for example by means of a cable 4, which implantable element can be formed as a heart pump, for example. The cable 4 is passed through the patient's skin by means of a feedthrough 5. The feedthrough 5 for example can also lead directly into one of the patient's blood vessels.

The cable 4 is used for the exchange of electrical signals between the control unit 1 and the implantable element 3, but also to supply power to the implantable element 3.

FIG. 2 shows a medical apparatus 2 with a control unit 1 and an implantable element 3 in the form of a symbolically illustrated heart pump, and a connection 4 in the form of a cable with a feedthrough 5 for feeding through the skin of a patient.

In FIG. 3, a housing 10 of the control unit 1 is shown schematically, which housing is made of a material not permeable for electromagnetic radiation, typically a metal, such as sheet steel or sheet iron or aluminium. However, the housing 10 for example can also be made of a plastic material filled with metal particles.

A circuit board 11 is shown schematically within the housing 10, and components on the circuit board are indicated.

The electronic components of the control unit are connected to a radio module 12, which is used to transmit and/or to receive signals by means of radio via an antenna 13. In this context, radio is understood to mean all signal transmissions by electromagnetic waves, for example with use of known communication standards, such as Bluetooth, Zig-Bee, WLAN, GPRS, GSM, LTE, etc.

The antenna 13 is arranged outside the housing 10 on the side thereof facing away from the side 9, so that the patient's body, which lies against the side 9 of the housing 10, is shielded from the antenna 13 by the housing 10. The supply line 14 to the antenna 13 is guided through the housing 10 in an electrically insulated manner in a feedthrough 15. The antenna 13 will usually run at only a short distance from the housing wall of the housing 10 so as to be arranged in a space-saving manner and at the same time so as not to be conductively connected to the housing 10.

FIG. 4 shows that antennas, which are illustrated schematically here, can also be arranged within the housing 10. The housing 10 is for this purpose divided into a region 10a of the housing that has walls made of a material impermeable for electromagnetic radiation, for example a metal, and a part 10b, the walls of which are made of a material permeable for electromagnetic waves, for example a plastic.

The housing part 10b can be fitted onto the housing part 10a in the manner of a housing lid or a cap. The housing part 10b for example can be welded, glued or cast with the housing part 10a. The housing part 10b can also be sealed with respect to the housing part 10a by means of an inserted elastomer seal.

Three possible positions 13a, 13b, 13c of the antenna are indicated in FIG. 4. Further positions and orientations are conceivable.

FIG. 5, similarly to FIG. 4, shows a division of the housing 10 into two parts, wherein a cap 10c represents merely a housing corner of the entire housing 10. An antenna 13d is shown in a possible position in the region of the housing cap 10c. The antennas 13a, 13b, 13c, 13d are illustrated in FIGS. 4 and 5 in such a way that in this region the housing wall of the housing parts 10b, 10c is assumed to be transparent for the viewer.

FIG. 6 shows, in cross-section, a divided housing with a cap 10d made of a material permeable for electromagnetic waves. Two possible antenna constellations are shown in the region of the cap 10d and are both connected to a radio module 12, more specifically on the one hand the rod antenna 13e, and on the other hand a dipole antenna 13g, with two loops. The antennas 13e, 13g constitute alternative possibilities, wherein only one of the two antennas will actually be provided in the event of practical application.

A radio module 12 is shown within a housing 10 in each of FIGS. 7 and 8, which radio module is made completely of a material impermeable for electromagnetic waves, for example metal, wherein the radio module 12 is connected in each case to a rod antenna 13 secured externally on the housing 10. The rod antenna 13 is shown from different perspectives in FIGS. 7 and 8. The rod antenna 13 is disposed externally on the housing 10 and runs at a short distance, for example at a distance between 0.5 mm and 3 mm, from a housing edge 16 of the housing 10, parallel thereto.

In FIG. 9 an antenna 13f is shown, which is formed of two portions, wherein each of the portions runs parallel to a housing edge of the housing 10, and wherein the portions of the antenna 13f run at a right-angle to one another. An optimised emission characteristic of the antenna, uniformly distributed on all sides to the greatest possible extent, is hereby achieved.

FIG. 10 shows a constellation in which a housing 10 of the control unit is made entirely of a material impermeable for electromagnetic waves. A radio module 12 is arranged within the housing 10 and is connected to a dipole antenna 13g, which is arranged outside the housing 10. A separate cap 10d made of a material permeable for electromagnetic waves is fitted onto the housing 10. The antenna 13g is arranged in the gap between the wall of the housing 10 impermeable for electromagnetic waves/radio signals and the housing wall of the cap 10d. The antenna is hereby on the one hand not prevented from emitting signals and on the other hand is optimally protected against ambient influences.

The cap 10d can be glued or cast onto the housing 10 or can be connected to the housing 10 by means of an elastomer seal. The cap 10d can be fitted onto the housing 10 in a mechanically frictionally engaged manner or can be connected to the housing 10 by means of a screw connection.

FIG. 11 shows a housing 10 made predominantly of a metal. A radio module 12 and an antenna 13 are provided within the housing 10. A window 17 is provided on the housing side facing away from the side 9 of the housing 10, in which window the housing wall of the housing 10 is filled by a material 18 permeable for electromagnetic waves. The window 17 for example can be a rectangular or round cutout in the for example metallic material of the housing 10, wherein the cutout can be cast with the material 18, for example plastic, or can be filled in another way. For example, a component made of plastic and shaped in a complementary manner can be glued or fixed in the window 17, and as appropriate can be in a sealed manner inset by means of an elastomer seal. The antenna 13 is arranged in the region behind the window 17 and the material part 18 made of a material permeable for electromagnetic waves, in such a way that the antenna can emit radio signals outwardly through the window 17.

FIG. 12 shows a housing 10 with a housing part 10a made of metal, which has a window 17. Within the housing 10, there is arranged an antenna 13 behind the window 17, which antenna is connected to the radio module 12. The window 17 for example can remain open in the housing 10; however, it can also be closed by a lid 19 made of a material permeable for electromagnetic waves, wherein the lid is placed externally onto the housing 10a in such a way that it closes the window 17. The lid 19 can be glued onto the housing or can be screwed thereto by means of a screw connection, wherein a seal can be provided by means of an inserted elastomer seal.

In a further alternative, a further arrangement of the antenna 13g as dipole antenna is illustrated in FIG. 12, which antenna is arranged in a further housing part 10e fitted onto the housing part 10a, wherein the housing part 10e can be made of a plastic or an elastomer. The housing part 10e extends through an opening in the housing 10a into the interior thereof and is connected there to a retaining flange 10f. This can be made of the same elastomer as the rest of the housing part 10e and can be compressed or deformed in order to be introduced into the housing 10, such that an undercut is created on the housing part 10e, by means of which undercut the housing 10e is secured in the housing part 10a.

The housing part 10e has a feedthrough for the supply line from the radio module to the antenna 13g. The antenna 13g is thus arranged outside the housing part 10a which is electrically conductive/impermeable for electromagnetic waves, but is protected against external influences by the housing part 10e.

FIG. 13, in two alternatives, shows a housing 10 which can be made of a material impermeable for electromagnetic waves and which has at least one recess 20, 20' for receiving a radio module 12, 12' which can be plugged in. The radio module can be plugged into the recess 20, 20' in such a way that the majority of the volume of the radio module 12 is received in the recess, so that less than half the radio module protrudes beyond the contour of the housing 10. In the case of the module 12', this is formed in a manner complementary to the recess 20', so that it terminates with the outer contour of the housing 10 in the plugged-in-state.

The radio module 12, 12' has a housing made of a material permeable for electromagnetic waves. The antenna 13, 13a is arranged within the radio module 12, 12' either outside the housing 10 or in the region of the housing wall of the housing 10. The antenna 13, 13a is shielded by the housing 10 or for example also by the circuit board 11 from the patient's body arranged on the side 9 of the housing 10.

In FIG. 13 the line 4 with the feedthrough 5 is also illustrated in an exemplary manner, which line is connected within the housing 10 to the electronics of the control unit, in particular to the circuit board 11.

FIG. 14 shows a particular embodiment of the control unit with an inner housing 10 made of metal, in which there is arranged a radio module 12, 12', for example. The supply line to the corresponding antenna 13, 13f is guided through the housing wall of the housing 10 in an insulated manner. The antennas 13, 13f each connected to respective radio modules 12, 12' are arranged outside the housing 10, but within a housing 21 surrounding the housing 10 partially or completely, wherein the housing 21 is made of a material permeable for electromagnetic waves, in particular a plastic. Different positions of the antennas 13, 13f are indicated. Numeral 9 denotes the side of the housing 21 or of the housing 10 facing towards the patient's body.

The radio module 12, 12' can also be arranged outside the housing 10 in the housing 21 and connected to the antenna 13, wherein the radio module is preferably positioned in a region of the housing 21 shielded from the patient's body by the housing 10.

The antenna 13 and in one embodiment also the radio module 12 can be provided in a corner part 102 of the housing 21, which corner part for example can also be secured separately to the housing 21 and/or can be separated/removed therefrom, as is indicated in FIG. 14 by the dashed lines 100, 101. A communications module 12, 13 can thus be exchanged or retrofitted as required. The communications module can be inserted as a housing part into the rest of the housing 21 and can be secured there, for example by means of an adhesive bond, clamping or screwing device, or a latched connection.

The antenna 13 and/or the radio module 12 can be secured in the housing part 102, for example also cast therein. When the housing part 102 is joined to the rest of the housing 21, the antenna and/or the radio module can be connected to a plug connection on the housing 10 in order to produce an electrical connection of the radio module 12 to a power supply and a signal line in the housing 10 or a connection of the antenna 13 to a signal line in the housing 10.

FIG. 15 shows an embodiment in which a housing 10 made of a material impermeable for electromagnetic waves is coated with a material permeable for electromagnetic waves. A radio module 12 is arranged within the housing 10 and is connected to a dipole antenna 13g. Instead of the dipole antenna, a rod antenna can also be provided in various forms. The antennas are in each case embedded in the material of the coating 22, for example cast in or foamed in. The material of the coating 22 for example can be formed as plastic, in particular as a foam material, and/or also as an elastomer. Within the coating 22 the corresponding antenna 13g is electrically insulated from the material of the housing 10, for example a metal.

With the above-explained embodiments an antenna of a radio module in a medical apparatus can be arranged advantageously in or on a housing of a control unit, wherein on the one hand the patient's body is shielded from the antenna and on the other hand the antenna is well protected against external influences. The same is true for example for the arrangement of the antenna of a GPS module, which can be integrated into a control unit.

The invention claimed is:

1. A medical apparatus comprising:
 an implantable element; and
 a control unit for the implantable element, wherein the control unit is connected to the implantable element by a first connection, wherein the control unit is configured for arrangement outside a patient's body and has a patient side configured to face a patient's body, wherein the patient side of the control unit has a contact face configured to contact the patient's body,
 wherein the control unit includes a housing, an electromagnetic shielding, an antenna, and a radio module, wherein the electromagnetic shielding is located at least partially between the patient side of the control unit and all electromagnetic wave generating components of the control unit,
 wherein a region of the housing made of an electrically insulating material permeable for electromagnetic waves protrudes beyond a contour of a plurality of electrically conductive regions of the housing, wherein the antenna is arranged in a space between the electrically conductive regions of the housing and the region of the housing made of the electrically insulating material permeable for electromagnetic waves.

2. The medical apparatus according to claim 1, wherein the antenna is positioned at least in part on a side of the control unit that is opposite of the patient side.

3. The medical apparatus according to claim 1, wherein the antenna is arranged at least in part within the housing of the control unit behind the region of the housing made of the electrically insulating material permeable for electromagnetic waves or behind a window-like recess.

4. The medical apparatus according to claim 1, wherein the antenna runs at least sectionally parallel to a housing edge of at least one of the electrically conductive regions of the housing at a distance of at least 1 mm therefrom.

5. The medical apparatus according to claim 1, wherein the antenna is a dipole antenna.

6. The medical apparatus according to claim 1, wherein the antenna is arranged within the housing in or directly behind the region that is made of the electrically insulating material permeable for electromagnetic waves.

7. The medical apparatus according to claim 1, wherein the region made of the electrically insulating material permeable for electromagnetic waves completely surrounds the electrically conductive regions of the housing and/or is tightly joined together to the electrically conductive regions of the housing.

8. The medical apparatus according to claim 7, the region of the housing made of the electrically insulating material permeable for electromagnetic waves is glued, cast, or tightly connected by means of an elastomer seal to the electrically conductive regions of the housing.

9. The medical apparatus according to claim 1, wherein the implantable element is a heart pump.

10. The medical apparatus according to claim 1, wherein the electromagnetic shielding comprises the electrically conductive regions of the control unit or of the housing of the control unit.

11. The medical apparatus according to claim 1, wherein the antenna comprises a dipole antenna, which comprises two closed conductor loops or conductor faces.

12. The medical apparatus according to claim 1, wherein the antenna is provided in a corner part of the housing.

13. The medical apparatus according to claim 12, wherein the corner part is separately securable to the housing and/or is removable therefrom.

* * * * *